(12) United States Patent
Otsubo

(10) Patent No.: US 6,406,465 B1
(45) Date of Patent: Jun. 18, 2002

(54) DISPOSABLE DIAPER HAVING LOWER CONCAVITY

(75) Inventor: Toshifumi Otsubo, Kagawa-ken (JP)

(73) Assignee: Uni-Charm Corporation (JP)

(*) Notice: Subject to any disclaimer, the term of this patent is extended or adjusted under 35 U.S.C. 154(b) by 0 days.

(21) Appl. No.: 09/497,330

(22) Filed: Feb. 3, 2000

(30) Foreign Application Priority Data

Feb. 4, 1999 (JP) .......................... 11-027784

(51) Int. Cl.[7] .................................. A61F 13/15
(52) U.S. Cl. ............ 604/385.01; 604/378; 604/385.28; 604/385.26
(58) Field of Search .................. 604/378, 385.01, 604/385.19, 385.26, 385.28

(56) References Cited

U.S. PATENT DOCUMENTS

| | | | |
|---|---|---|---|
| 5,792,130 A | * 8/1998 | Widlund et al. | 604/385.1 |
| 6,132,409 A | * 10/2000 | Vogt et al. | 604/348 |
| 6,152,907 A | * 11/2000 | Widlund et al. | 604/385.08 |
| 6,254,583 B1 | * 7/2001 | Coates | 604/385.1 |

* cited by examiner

Primary Examiner—John G. Weiss
Assistant Examiner—Jacqueline F. Stephens
(74) Attorney, Agent, or Firm—Baker & Daniels

(57) ABSTRACT

A disposable diaper includes a laminated panel having a topsheet, a backsheet and an absorbent core disposed therebetween to configure a front waist region, a rear waist region and a crotch region; the laminated panel is provided with a concavity extending a longitudinal center line of the panel from the rear waist region to the crotch region and depressed toward a surface of the panel remote from the wearer's skin.

7 Claims, 4 Drawing Sheets

DISPOSABLE DIAPER HAVING LOWER CONCAVITY

BACKGROUND OF THE INVENTION

This invention relates to a disposable diaper for absorption and containment of body wastes.

Japanese Utility Model Application Disclosure No. 1993-86320 discloses a disposable diaper comprising a liquid-pervious topsheet, a liquid-impervious backsheet and an absorbent core disposed between these two sheets. The absorbent core is provided in a crotch region with an body wastes receiving pocket. The pocket comprises a concavity depressed downward from the upper surface of the absorbent core and a protuberance rising from the upper surface of the absorbent core to define a peripheral edge of the concavity.

Japanese Utility Model Application Disclosure No. 1994-21624 discloses a disposable diaper comprising a liquid-pervious topsheet, a liquid-impervious backsheet and an absorbent core disposed between these two sheets. The absorbent core is provided in a hip region with a concavity serving to receive body wastes.

Both of these proposals intend to form the absorbent core with the concavity with or without the annular protuberance encircling it and thereby to hold solid body wastes such as faeces in the concavity.

However, various problems may be encountered by such known diapers depending on situations. It is assumed that the body wastes pocket formed on the absorbent core in the crotch region or the body wastes receiving concavity formed on the absorbent core in the hip region various problems misses the proper position to receive the body wastes. In this case, the solid body wastes can not be received by the pocket or concavity. If the liquid-permeability of the topsheet defining the upper surface of the diaper is not sufficient, the liquid body wastes such as loose passage due to diarrhea once having been received by the concavity or pocket may flow back again up to the surface of the topsheet and spreads sideways. If the absorbent core is relatively thin as achieved by a recent technical progress, it will be difficult to form the concavity or pocket adapted to receive a desired amount of body wastes.

SUMMARY OF THE INVENTION

An object of this invention is to provide a disposable diaper so improved that body wastes may be received and held within the diaper without forming the absorbent core with both the concavity and the protuberance.

According to this invention, there is provided a disposable diaper comprising a laminated panel having a liquid-pervious topsheet, a liquid-impervious backsheet and a liquid-absorbent core disposed between the topsheet and the backsheet to configure a front waist region, a rear waist region and a crotch region extending between the front and rear waist regions; the laminated panel being provided with a concavity having a pair of joined edges extending along a longitudinal center line of the panel from the rear waist region to the crotch region and depressed toward a surface of the panel remote from the wearer's skin, the concavity comprising a pair of sections divided along the joined edges and defining a space of a given shape between the joined edges before the joined edges are joined together, and the concavity which is formed as the pair of sections being drawn near toward each other and the joined edges being joined together on the longitudinal center line.

According to one embodiment of this invention, a transverse dimension of the space gradually decreases from the rear waist region toward the crotch region and a depth of the concavity gradually increases from the rear waist region toward the crotch region.

According to another embodiment of this invention, a pair of leak-proof cuffs each having a free side edge provided with an elastic member joined under tension thereto and a proximal side edge joined to the upper surface of the topsheet so that the elastic member biases the cuff to rise on the upper surface of the topsheet, wherein the pair of cuffs extend in the longitudinal direction in the vicinity of the transversely opposite side edges of the absorbent core and wherein a dimension by which the pair of cuffs gradually decreases from the crotch region toward the rear waist region.

According to still another embodiment of this invention, the free side edges of the leak-proof cuffs come in contact with each other in the rear waist region.

According to further another embodiment of this invention, longitudinally opposite ends of the leak-proof cuffs are collapsed onto the inner side of the diaper and joined to the upper surface of the topsheet.

DETAILED DESCRIPTION OF THE PREFERRED EMBODIMENTS

A disposable diaper according to this invention will be described in more details with respect to the accompanying drawings.

Figure 1:
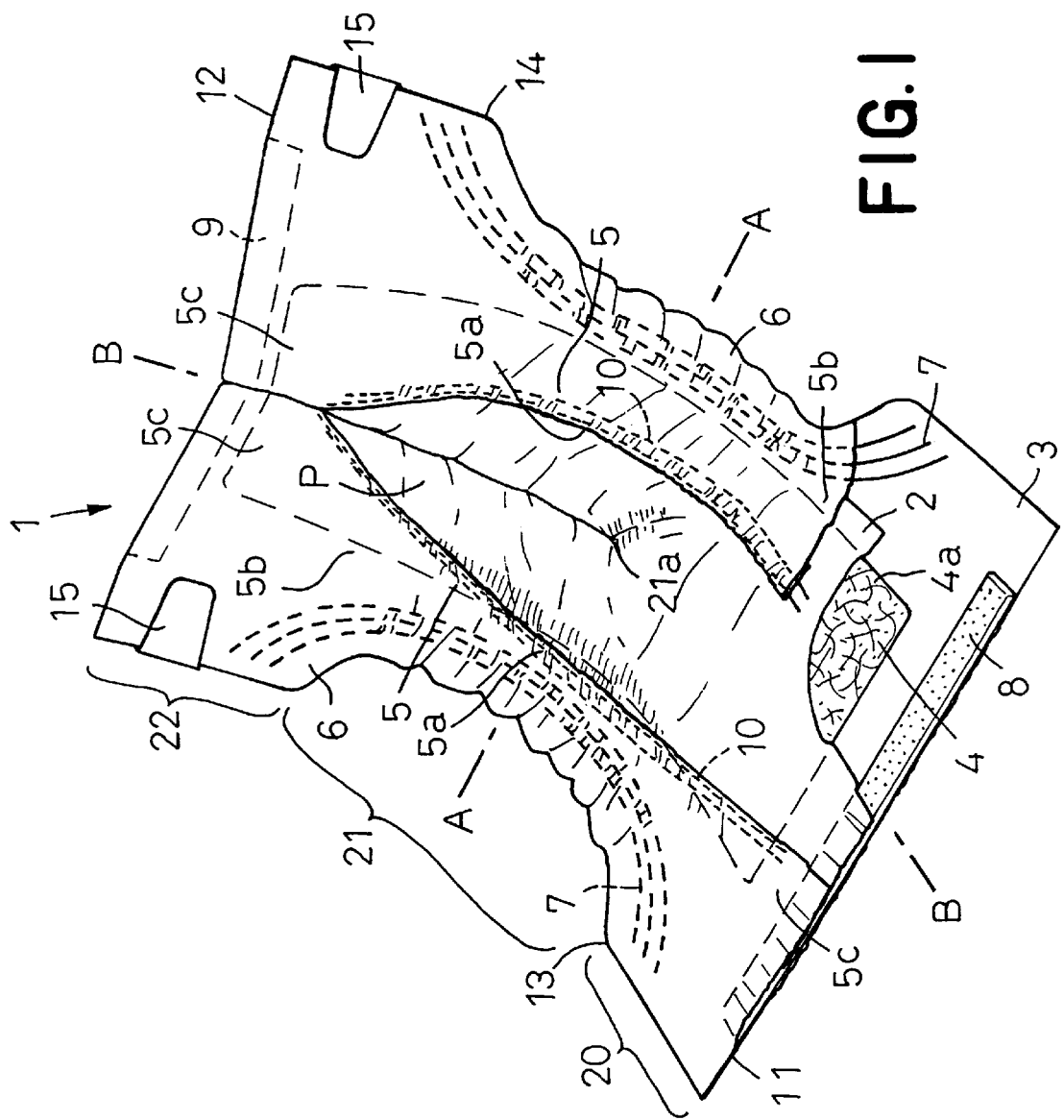
FIG. 1 is a perspective view showing a partially cutaway disposable diaper according to a typical embodiment of this invention.
Figure 2:
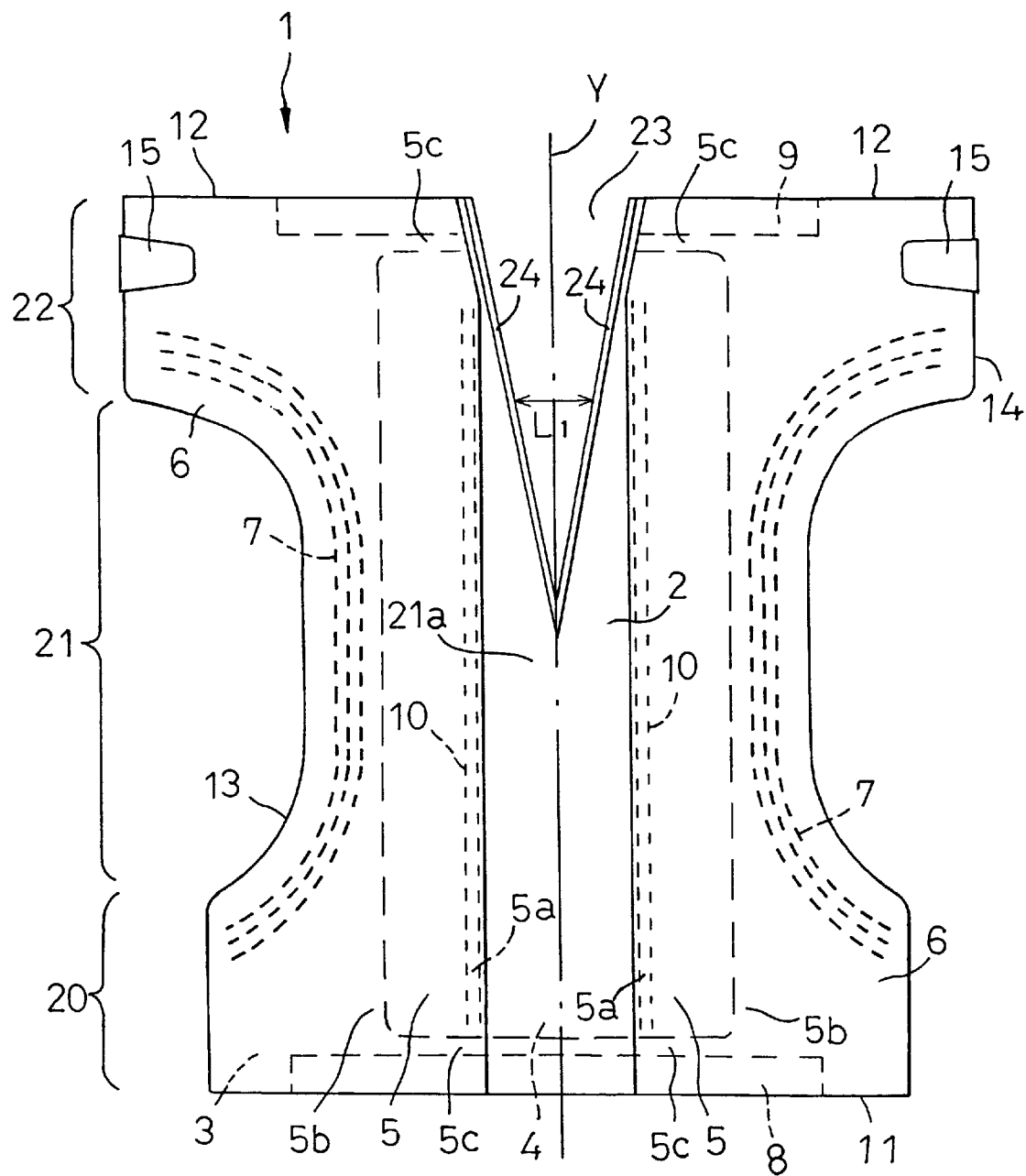
FIG. 2 is a plan view showing the diaper as before transversely opposite side edges of a cutout are joined to each other.

FIG. 1 is a perspective view showing a partially cutaway disposable diaper and FIG. 2 is a plan view showing the diaper as before transversely opposite side edges 24 (the edges to be joined together) of a cutout 23 (space) are joined to each other. The diaper includes a laminated panel 1 which comprises, in turn, a liquid-pervious topsheet 2, a liquid-impervious backsheet 3 and a liquid-absorbent core 4 disposed between the topsheet 2 and the backsheet 3. The liquid-absorbent core 4 is joined to the inner surface of at least one of the two sheets 2, 3. The panel 1 is provided with a pair of leak-proof cuffs 5 extending in the longitudinally of the panel 1. Configurationally, the panel 1 has a front waist region 20, a rear waist region 22 and a crotch region 21 extending between the front and rear waist region 20, 22 as viewed in the longitudinal direction of the panel 1. The panel 1 is contoured by transversely opposite side edges 13, 14 curved inwardly of said panel 1 in the crotch region 21 and longitudinally opposite ends 11, 12 extending in the transverse direction so as to intersect the side edges 13, 14.

The panel is provided with a pocket P (concavity) extending from the vicinity of the longitudinal middle 21a of the crotch region 21 to the vicinity of the end 12 of the rear waist region 22 and depressed toward the surface of the panel 1 being remote from the wearer's skin. The pocket P is formed by bonding transversely opposite side edges 24, 24 of the cutout 23 which extend from the rear waist region 22 toward the crotch region 21.

The cutout 23 is V-shaped and extends from the rear waist region 22 to the vicinity of the longitudinal middle 21a of the crotch region 21 symmetrically about a longitudinal center line Y longitudinally extending to bisect a transverse dimension of the panel 1. A dimension L by which the transversely opposite side edges 24, 24 of the cutout 23 are spaced from said longitudinal center line Y, respectively, gradually decreases from the rear waist region 22 toward the crotch region 21. It should be understood that the cutout 23 is not limited to the V-shape but may be also of U-shape having acute or obtuse apex on said longitudinal middle 21a of the crotch region 21.

The panel 1 is further provided with a pair of side flaps 6, 6 extending outward from transversely opposite side edges 4a of the absorbent core 4, each being relatively narrow in the crotch region 21 and relatively wide in the front and rear waist regions 20, 22. The side flaps 6, 6 are provided with a plurality of elastic members 7, 7, respectively, extending along the side edges 13, 14 of the panel 1 and joined with a tension to the respective side flaps 6, 6. These elastic members 7, 7 are intended to be associated with leg-openings.

The panel 1 is additionally provided on its inner surface with a pair of leak-proof cuffs 5, 5 extending longitudinally in the vicinity of the side edges 4a, 4a of the absorbent core 4. The cuffs 5 have their proximal edges 5b, 5b joined to the upper surface of the topsheet 2 and their longitudinally opposite ends 5c, 5c lying short of the corresponding ends of the panel 1. These longitudinally opposite ends 5c, 5c are collapsed onto and joined to the upper surface of the topsheet 2. The leak-proof cuffs 5, 5 are provided along their free side edges 5a, 5a with elastic members 10, 10 joined under tension to the free side edges 5a, 5a so that the elastic members 10, 10 contract as the panel 1 is longitudinally curved with the inner surface of the panel 1 inside. Contraction of the elastic members 10, 10 causes the cuffs 5, 5 to rise on the panel 1 and simultaneously causes the free side edges 5a, 5a of the cuffs 5, 5 to form gathers. A dimension by which the pair of cuffs 5, 5 are spaced from each other gradually decreases from the crotch region 21 toward the rear waist region 22. In the rear waist region 22, the free side edges 5a, 5a of the cuffs 5, 5 come in contact with each other so that these cuffs 5, 5 surround the pocket P in the rear waist region 22.

In the front and rear waist regions 20, 22, the panel 1 is provided along the longitudinally opposite ends 11, 12 with a pair of film-like elastic members 8, 9, respectively, extending transversely of the panel 1. These film-like elastic members 8, 9 are intended to be associated with a waist-opening. These film-like elastic members 8, 9 are disposed between the topsheet 2 and the backsheet 3 and joined under tension to at least one of these sheets 2, 3. FIG. 1 shows these elastic members 8, 9 having their tension relieved so that the gathers are formed along the transversely opposite side edges 13, 14 of the panel 1 in the crotch region 21 as well as along the longitudinally opposite ends 11, 12 of the panel 1.

In the rear waist region 22, the transversely opposite side edges 13, 14 are provided with a pair of tape fasteners 15, 15, respectively, extending from the side edges 13, 14 inward transversely of the panel 1. These tape fasteners 15, 15 have their proximal ends joined to the rear waist region 22 and their free ends coated with adhesive agent. In the front waist region 20, the outer surface of the panel 1 is provided with a pair of fastening zones each in the form of target tape so that the respective tape fasteners 15, 15 may be fastened to the corresponding pieces of target tape by means of the adhesive agent applied on the inner surfaces of the tape fasteners 15, 15. In this manner, a waist-opening and a pair of leg-openings are formed (not shown).

Figure 3:
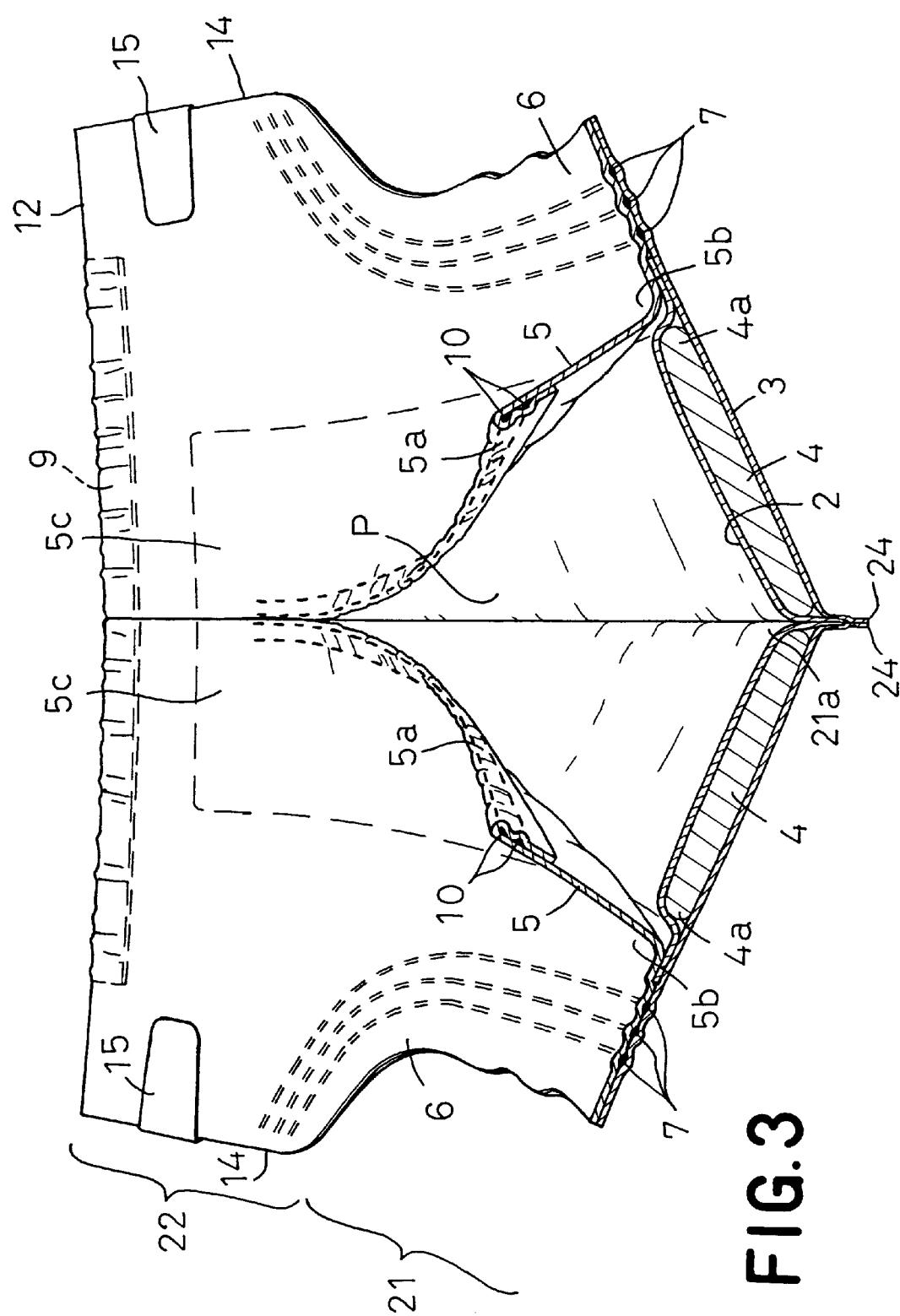
FIG. 3 is a perspective view showing the diaper partially in a sectional view taken along a line A—A in FIG. 1.
Figure 4:
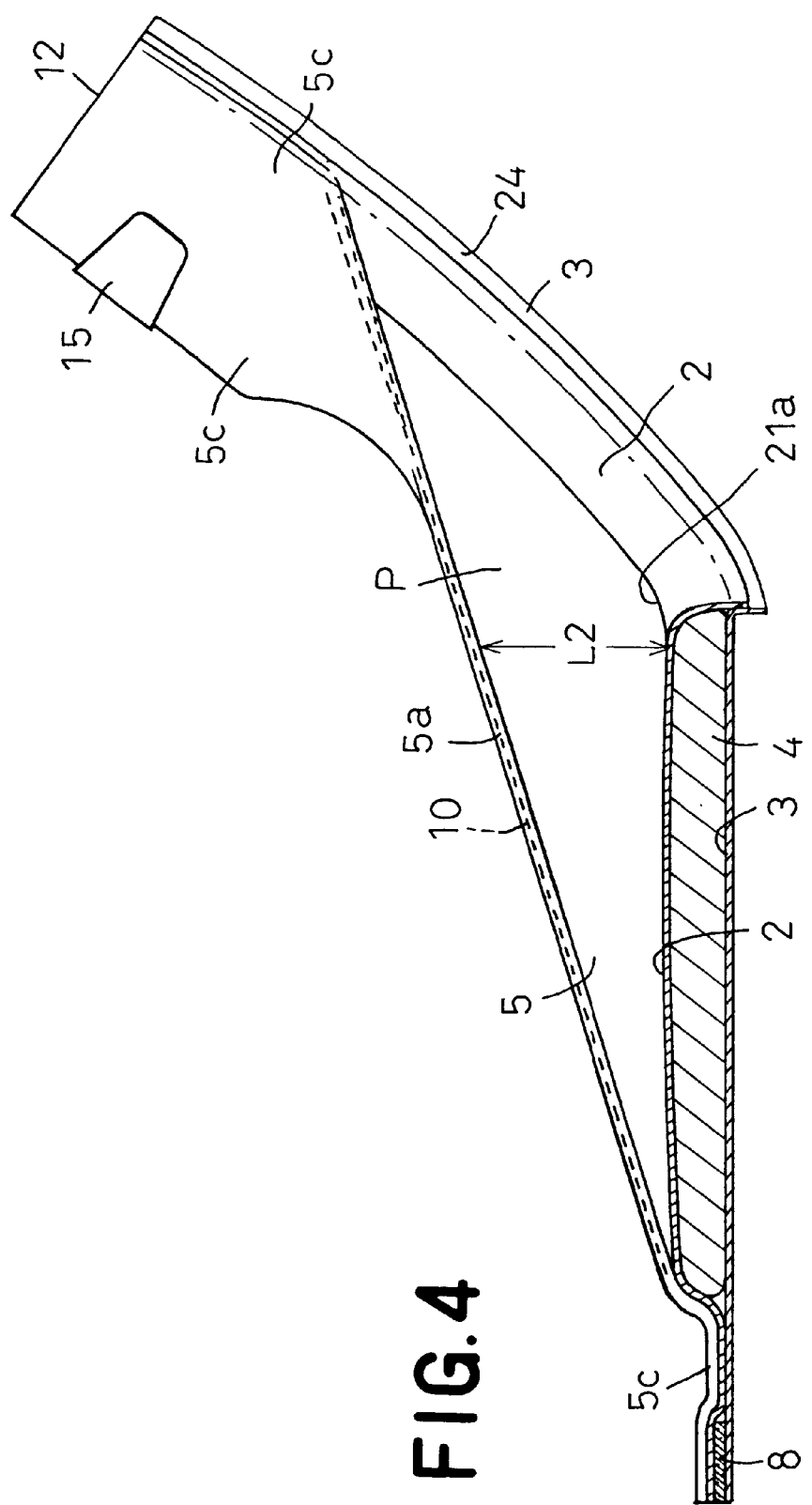
FIG. 4 is a sectional view taken along a line B—B in FIG. 1.

FIG. 3 is a perspective view showing the panel 1 partially in a sectional view taken along a line A—A in FIG. 1 and FIG. 4 is a sectional view taken along a line B—B in FIG. 1. FIG. 3 shows the cuffs 5, 5 as rising on the inner surface of the panel 1. Along the transversely opposite side edges 24, 24 of the cutout 23, the upper surface sections of the topsheet 2 are joined to each other and the upper surface sections of the backsheet extending downward beyond the topsheet 2 are also joined to each other.

In the panel 1, the transversely opposite side edges of the topsheet 2 lie in the vicinity of the respective side edges 4a, 4a of the absorbent core 4 and the transversely opposite side edges of the backsheet 3 further extend outward beyond the respective side edges of the topsheet 2. The pair of cuffs 5, 5 are formed by a nonwoven fabric extending outward from the transversely inner zone of the panel 1. Along the free side edges 5a, 5a of the respective cuffs 5, 5, the nonwoven fabric is folded back onto the inner surface of the panel 1 to wrap the elastic members 10, 10 and these elastic members 10, 10 are intermittently joined to the respective cuffs 5, 5. The cuffs 5, 5 are joined to the respective side edges of the backsheet 3 in their zones extending outward from the proximal edges 5b, 5b transversely of the panel 1. While the free side edges 5a, 5a of the respective cuffs 5, 5 may be joined together or not joined together in the rear waist region 22, they are preferably joined together in the rear waist region 22 in order that a leak of body wastes occurring in the rear waist region 22 can be more reliably avoided.

Each side edge zone of the backsheet 3 is combined with a portion of the cuff 5 to form each side flap 6 and the elastic member 7 for the leg-opening disposed between them is intermittently joined to at least one of the backsheet 3 and the cuff 5.

As will be apparent from FIG. 4, a depth L2 of the pocket P gradually increases from the rear waist region 22 to the crotch region 21 and the depth L2 is maximum in the vicinity of the middle zone 21a of the crotch region 21.

The topsheet 2 may be formed by a liquid-pervious sheet such as a nonwoven fabric or a porous plastic film, preferably a sheet which is not only liquid-pervious but also hydrophobic. The backsheet 3 may be formed by a liquid-impervious plastic film or a laminate of such plastic film and a hydrophobic nonwoven fabric, preferably a breathable and liquid-impervious sheet. The leak-proof cuffs 5 may be formed by breathable a nonwoven fabric, preferably a breathable and liquid-impervious nonwoven fabric sheet. The nonwoven fabric may be selected from a group consisting of a spun bond nonwoven fabric, a spun lace nonwoven fabric and a melt blown nonwoven fabric, each comprising fibers having a basis weight of 5~150 g/m$^2$. The absorbent core 4 comprises a mixture of fluff pulp and superabsorptive polymer grains compressed to a desired thickness and entirely covered with a water-pervious sheet such as tissue paper. Bonding of these members may be performed by means of suitable adhesive agent such as hot melt adhesive, glue or heat-sealing technique.

With the disposable diaper according to this invention, it is possible to form the pocket adapted to receive and hold body wastes within the diaper without forming the absorbent core with the concavity and the protuberance. For solid body wastes, the body wastes will be received and held in the deepest zone of the pocket in the vicinity of the middle of the crotch region. It is avoided thereby that the body wastes might leak back from the diaper. For liquid body wastes, the body wastes will flow into the deepest zone of the pocket and be absorbed by the absorbent core through the topsheet and it is not apprehended that the body wastes might flow back to the upper surface of the topsheet and spread therethrough.

The dimension by which the pair of leak-proof cuffs are spaced from each other gradually decreases from the crotch region toward the rear waist region in which the free side edges of the cuffs come in contact with each other to surround the pocket. In this manner, the cuffs serve as barriers which are effective to avoid leak of the body wastes in the rear waist region.

What is claimed is:

1. A disposable diaper comprising:
   a laminated panel having;
      a liquid-pervious topsheet;
      a liquid-impervious backsheet;
      a liquid-absorbent core having an upper surface and being disposed between said topsheet and said backsheet so that said liquid-pervious topsheet contacts the entire upper surface of said liquid-absorbent core;
      a front waist region;
      a rear waist region; and
      a crotch region extending between said front and rear waist regions,
   said laminated panel being provided concavity,
      said concavity being formed by joining together sections of transversely opposite side edges of said laminated panel which otherwise divert from one another along a centerline of the laminated panel.

2. The diaper according to claim 1, wherein said sections of the transversely opposite side edges which are joined together otherwise converge along a direction that extends from said rear waist region toward said crotch region and when said sections of the transversely opposite side edges are joined together said concave pocket has a depth which gradually increases from said rear waist region toward said crotch region.

3. The diaper according to claim 2, further comprising a pair of leak-proof cuffs each having a free side edge provided with an elastic member joined under tension thereto and a proximal side edge joined to the upper surface of said topsheet so that said elastic members bias said leak-proof cuffs and cause them to rise on said upper surface of said topsheet, said pair of leak-proof cuffs extending in said longitudinal direction in the vicinity of the transversely opposite side edges of said absorbent core and said pair of leak-proof cuffs gradually converge toward one another alone a direction that extends from said crotch region toward said rear waist region.

4. The diaper according to claim 3, wherein the free side edges of said leak-proof cuffs contact each other in said rear waist region.

5. The diaper according to claim 3, wherein longitudinally opposite ends of said leak-proof cuffs are collapsed onto an inner side of said diaper and joined to the upper surface of said topsheet.

6. The diaper according to claim 1, wherein the laminated panel includes a pocket having continuous sides which extend from the rear waist region to the front waist region.

7. The diaper according to claim 1, wherein the laminated panel includes a pocket that has a width that increases from the rear waist region toward the crotch region.

* * * * *

UNITED STATES PATENT AND TRADEMARK OFFICE
CERTIFICATE OF CORRECTION

PATENT NO. : 6,406,465 B1
DATED : June 18, 2002
INVENTOR(S) : Toshifumi Otsubo

It is certified that error appears in the above-identified patent and that said Letters Patent is hereby corrected as shown below:

<u>Column 6,</u>
Line 20, change "alone" to -- along --

Signed and Sealed this

First Day of October, 2002

Attest:

Attesting Officer

JAMES E. ROGAN
*Director of the United States Patent and Trademark Office*